(12) United States Patent
Keller

(10) Patent No.: US 7,785,623 B2
(45) Date of Patent: Aug. 31, 2010

(54) COMPOSITIONS AND METHODS USEFUL FOR THE REDUCTION OF FINE LINES AND WRINKLES

(76) Inventor: Brian C. Keller, 1111 James Donlon Blvd., #2034, Antioch, CA (US) 94509

(*) Notice: Subject to any disclaimer, the term of this patent is extended or adjusted under 35 U.S.C. 154(b) by 286 days.

(21) Appl. No.: 10/263,358

(22) Filed: Oct. 1, 2002

(65) Prior Publication Data

US 2004/0062780 A1 Apr. 1, 2004

(51) Int. Cl.
*A61K 9/127* (2006.01)
(52) U.S. Cl. .................. 424/450; 424/401; 604/20
(58) Field of Classification Search .............. 424/400, 424/401, 450, 78.02, 78.03; 514/844, 944, 514/946; 624/20
See application file for complete search history.

(56) References Cited

U.S. PATENT DOCUMENTS

| | | | | |
|---|---|---|---|---|
| 4,149,533 | A | * 4/1979 | Ishikawa et al. | 604/20 |
| 5,492,935 | A | 2/1996 | Yu et al. | 514/703 |
| 5,720,973 | A | * 2/1998 | Rosenberg et al. | 424/450 |
| 5,741,515 | A | * 4/1998 | Ciceri et al. | 424/450 |
| 5,834,016 | A | * 11/1998 | Naeff et al. | 424/450 |
| 5,964,726 | A | 10/1999 | Korenstein et al. | 604/20 |
| 5,993,180 | A | 11/1999 | Westerhof et al. | 417/571 |
| 6,048,545 | A | * 4/2000 | Keller et al. | 424/450 |
| 6,302,874 | B1 | 10/2001 | Zhang et al. | 604/522 |
| 6,308,413 | B1 | 10/2001 | Westerhof et al. | 30/41 |
| 6,348,214 | B1 | 2/2002 | Onyuksel et al. | 424/450 |
| 6,610,322 | B1 * | 8/2003 | Keller et al. | 424/450 |
| 2001/0056255 | A1 | 12/2001 | Kost et al. | 604/22 |

FOREIGN PATENT DOCUMENTS

WO   WO 9851278   * 11/1998

OTHER PUBLICATIONS

International Search Report, for PCT patent application No. PCT/US03/31093, 4 pages.
Gangarosa et al. "Conductivity of Drugs Used for Iontophoresis" J. Pharm. Sci. 67(10):1439-1443 (1979).
Gangarosa et al. "Pharmacologic Management of TMJ-MPDS" Ear, Nose & Throat 61:30-41 (1982).
Gangarosa et al. "Iontophoresis (Ionto) for Pain Relief in Postherpetic Neuralgia (PHN): Double-Blind Trials" Proc. Soc. Exper. Bio. & Med. 181(3):476 (1986).
Oikarinen. "The Aging of Skin: Chronoaging Versus Photoaging" Photodermatol. Photoimmunol. Photomed. 7:3-4 (1990).
Rädler, Jo. et al. "Structure and Interfacial Aspects of Self-Assembled Cationic Lipid-DNA Gene Carrier Complexes" Langmuir 14:4272-7283 (1998).
Sloan et al. "Iontophoresis in Dermatology" J. Am. Acad. Derm. 15(4, pt 1):671-684 (1986).
Singh and Roberts. "Transdermal Delivery of Drugs by Iontophoresis: A Review" Drug Design & Delivery 4:1-12 (1989).
Tyle, P. "Iontophoretic Devices for Drug Delivery" Pharm. Res. 3(6):318-326 (1986).

* cited by examiner

*Primary Examiner*—Gollamudi S Kishore
(74) *Attorney, Agent, or Firm*—Morrison & Foerster LLP

(57) ABSTRACT

A cosmetic treatment process is provided herein useful for reducing fine lines, wrinkles, or fine lines and wrinkles. The process comprises contacting a composition to an area of the skin or tissue of a subject, wherein the composition comprises a substance encapsulated within a lipid vesicle comprising a lipid having one or more polyethylene glycol (PEG) chains. The lipid vesicle has a charged surface, and an electric voltage is applied directly to the area of the skin that is contacted with the composition, whereby fine lines, wrinkles, or fine lines and wrinkles are reduced.

24 Claims, 6 Drawing Sheets

PEG-12 Glyceryl Dioleate

COMPOSITIONS AND METHODS USEFUL FOR THE REDUCTION OF FINE LINES AND WRINKLES

FIELD OF THE INVENTION

The invention relates to administration of cosmetic substances, encapsulated within a lipid vesicle, through the application of an electrical current.

BACKGROUND OF THE INVENTION

Many personal care products currently available to consumers are directed primarily to improving the health and/or physical appearance of the skin. Among these skin care products, many are directed to delaying, minimizing or even eliminating skin wrinkling and other histological changes typically associated with the aging of skin or environmental damage to human skin.

Extrinsic or intrinsic factors may result in the thinning and general degradation of the skin. For example, as the skin naturally ages, there is a reduction in the cells and blood vessels that supply the skin. There is also a flattening of the dermal-epidermal junction which results in weaker mechanical resistance of this junction. See, for example, Oikarinen, "The Aging of Skin: Chronoaging Versus Photoaging," Photodermatol. Photoimmunol. Photomed., vol. 7, pp. 3-4, 1990.

Existing therapies useful for reducing or eliminating fine lines and wrinkles are often invasive, cumbersome and/or expensive. Such examples include exfoliation (through laser resurfacing, chemical peels, dermabrasion and cold ablation); implants (comprising silicone, microlipoinjection, gore-tex and collagen); and muscle relaxants such as Botulinum. Plastic surgery may also be employed for removing wrinkles.

Existing noninvasive methods of reducing fine lines and wrinkles in subjects generally involve the application of a topical cream or other composition. These methods may utilize many of a variety of ingredients, however, the penetration of these ingredients past the stratum corneum is limited. Therefore, the effect that these creams or compositions have on the collagen network is negligible due to limited penetration and delivery.

Iontophoresis is a technique that has been used to enhance the penetration of topically applied drugs or other substances on skin and mucous membranes through the use of electric current. This technique is cumbersome, in part, because it requires placing separate electrodes on a person, one for delivery of an electric current, the other required to ground the electric current. Examples of such use include: Gangarosa et al., *J. Pharm. Sci.* (October 1979) 67(10):1439-1443; Gangarosa et al., *Ear. Nose & Throat* (December 1982) 61:30-41; Gangarosa et al., *Proc. Soc. Exper. Bio. & Med.* (1986) 181 (3):476; Tyle, P., *Pharm. Res.* (1986) 3(6):318-326; Sloan et al., *J. Am. Acad. Derm.* (October 1986) 15(4, pt 1):671-684; Sloan et al., *Drug Design & Delivery* (1989) 4:1-12; and Kost, J. et al., U.S. patent application Ser. No. 20010056255 (filed Dec. 27, 2001) (iotophoresis combined with ultrasound); and Keller et al., U.S. Pat. No. 6,048,545. In addition, in examples where iontophoresis contemplates the use of liposomes, these are exclusively phospholipid-based liposomes. Relatedly, the use of pulsed current to load molecules into a membrane vesicle in cultured cells has been described in U.S. Pat. No. 5,964,726.

Accordingly, there is still a need to overcome difficulties that are encountered in therapeutic or experimental administration of compositions which have a positive effect on a subject's collagen support network and which do not involve cumbersome and invasive alternative methods of wrinkle reduction.

SUMMARY OF THE INVENTION

A cosmetic treatment process is provided herein for reducing fine lines, wrinkles, or fine lines and wrinkles, comprising contacting a particular composition to an area of the skin or tissue of a subject. This process involves the use of a composition which may be composed of a substance (e.g., vitamin A, vitamin E, or a combination thereof) encapsulated within a lipid vesicle. The lipid vesicle preferably comprises a lipid which has one or more polyethylene glycol (PEG) chains (frequently dioleoglycerol-PEG-12), and a charged surface. In this process an electric voltage may then be applied directly to the area of the skin where the composition was contacted. The application of the voltage may either be subsequent to contact of the skin with the composition or simultaneous with this contact. As provided below, through the use of the process fine lines, wrinkles, or fine lines and wrinkles are reduced.

In one aspect an ionic moiety may be incorporated in the presently described lipid vesicles. The ionic moiety may have a positive or negative charge or may be a polar lipid vesicle comprising both positive and negative charges. In a related aspect, the lipid vesicle may have a positively or negatively charged surface, or a polar surface. The charge on the surface of the lipid vesicle may be due to a moiety encapsulated in the lipid vesicle or due to a moiety bound to the lipid vesicle. In another aspect, representative compositions may be comprised of an assortment of lipid vesicles, each having positive or negative charges.

The present description provides lipids in suspension which may spontaneously form liposomes upon adding liquid lipid to an aqueous solution. The lipids may comprise a single lipid or a mixture of lipids (which include one or more lipids comprising a polyethyleneglycol (PEG) chain) that have appropriate packing parameters, and that has a melting temperature which allows it to be in liquid form when mixed with the aqueous solution. Such liposome suspensions are useful for a variety of purposes, including the delivery of agents which aid in reducing fine lines and wrinkles.

Direct or alternating currents may be administered according to the present disclosure. However, regardless of the type of current delivered, the charge on the surface of the lipid vesicles within the compositions of the present disclosure frequently is the same as the charge of the current being administered. Occasionally, when an alternating current is administered, the composition may be comprised of positively charged lipid vesicles, polar lipid vesicles, and/or a combination of positively and negatively charged lipid vesicles.

According to another aspect of the present disclosure, a variety of treatment regimen are provided which are useful for the reduction of fine lines and/or wrinkles in a subject. Generally, the application of a voltage between about 0.5 Volts to about 20 Volts, and frequently between about 0.05 Volts to about 10 Volts, for a duration between about 1 to about 30 minutes is subsequent to, or concurrent with, the contact of the skin of a subject with representative compositions of the present disclosure.

In addition, the present disclosure describes representative devices for the administration of an electric voltage, in the range described above, to the skin of a subject. In one aspect these devices comprise one or more conductive surfaces, a body, and a mechanism useful for notifying a user of the device that the device is administering an electric voltage. If the device comprises two or more conductive surfaces, the first of the conductive surfaces is meant for direct contact with the composition on the skin of a subject (in an area of the skin where fine lines and/or wrinkles is desired), and any additional conductive surfaces are meant for contact with another part of the subject's body, for example, the hand(s) or finger(s) of the subject separate from the point of contact of the first conductive surface with the subject. All of the conductive surfaces may be situated on the body of the device represented by an integrated unit. In addition, the body of the device may be designed to hold one or more batteries which may provide the power source for the electric voltage, which power source may travel through an inverter prior to administration of the electric voltage. In another aspect, the device may be powered by an alternating current delivered through conventional means, i.e., a standard wall outlet.

In another aspect, the present disclosure contemplates kits containing a device and compositions useful in the disclosed methods. Frequently such kits may contain a one or more compositions useful in the present methods.

DETAILED DESCRIPTION OF THE INVENTION

Figure 1:
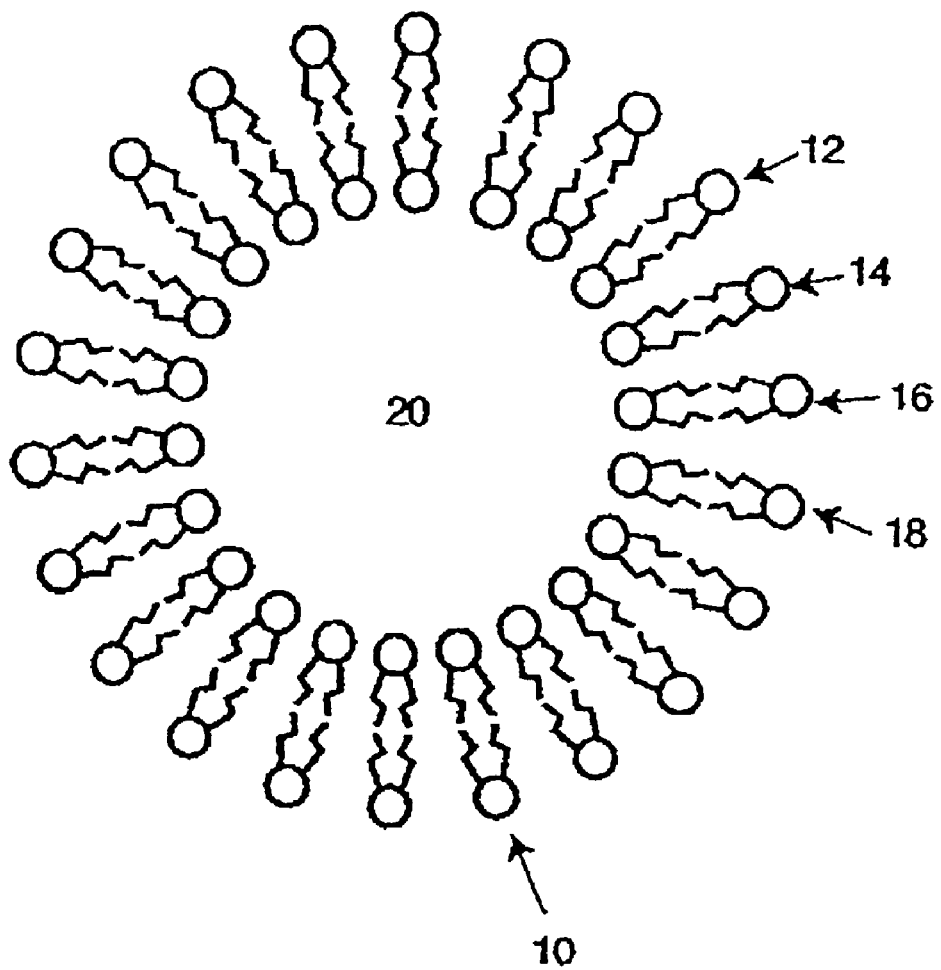
FIG. 1 is a diagram depicting the cross-section of a liposome made of lipid molecules.

Featured herein is a method useful for driving a substance having a positive or negative charge into or through tissue and/or skin and past the stratum corneum layer. Thus, this method can be used for dermal and transdermal delivery of a substance or composition, including the delivery of a substance useful for the reduction of fine lines and/or wrinkles in a subject. Accordingly, the method can be used for delivery of substances for human use.

In the present methods, a device with one or more conducting surfaces is placed in contact with the tissue or skin of a subject and an electric current is applied. Frequently, the tissue or skin is treated or contacted with a composition prior to contacting the conducting surface with the tissue or skin and application of a particular voltage. Representative compositions provided herein are useful for the reduction of fine lines and/or wrinkles. Any sort of method or tools known in the art are useful for contacting a composition with the skin of a subject, for example, with applicators known in the art, by hand, with the conducting surface of the device, and others.

When the tissue or skin is contacted with the composition prior to application of the voltage, the first conducting surface is contacted with the area of the skin or tissue that has been contacted with the composition. If, however, the contact of the composition and application of the voltage are simultaneous then the first conducting surface may contact an area of the skin where fine line and/or wrinkle reduction is desired.

Determining the actual amount of wrinkle and/or fine line reduction obtained through the use of the present invention may be by any method commonly used in the art, such as, for example, the Glogau Photoaging Classification, surface roughness measurement, disposable position sensors, strain gauge, stretch tests, and the silicone imprint method. In addition, tests such as these are frequently not desired (or otherwise not needed to determine results) by subjects which are able to take visual notice of the softening of fine lines and reduction of wrinkles as a result of the use of the present methods.

The term "wrinkle" as used herein refers to a small ridge, furrow or crease in the skin, especially when due to age, care, or fatigue. In general, wrinkles are associated with the degeneration of dermal elastic tissue. The term "fine line" as used herein may be defined in relation to the term "wrinkle" in terms of degree; the underlying pathology of both of these terms, however, is the same for purposes of the present invention. Generally, a wrinkle is reflective of more severe damage to dermal tissue than a fine line. In one aspect, a fine line may be defined as a shallower wrinkle.

The present method may be defined as a means of enhancing the flux of ionic compounds through the skin of a subject, by the application of an electric current across it. The skin is a multi-layered organ delimiting the body which is constituted of several layers. For purposes of the present invention, the outermost layer (stratum corneum) presents the main barrier to sub-dermal transport of ingredients and biologically active materials. The application of electric current, however, produces an increased penetration of molecules through this barrier. The two principal mechanisms by which the present technique enhances molecular transport across the skin are:

(a) iontophoresis, in which a charged ion is repelled from an electrode of the same charge, and (b) electroosmosis, the convective movement of solvent that occurs through a charged "pore" in response to the preferential passage of counter-ions when the electric field is applied.

The isoelectric point of the skin is about 4; therefore, under physiological conditions, with the surface of the skin also buffered at or near 7.4, the membrane has a net negative charge and electroosmotic flow is from anode (+) to cathode (−). Electroosmosis has been used as a means to augment the transdermal migration of charged and/or polar molecules, which generally have low passive permeability.

Lipids and Liposomes

Liposomes are vesicles composed of membrane-like lipid layers surrounding aqueous compartments. The lipid layers have a hydrophilic head and a lipophilic tail. In aqueous solution they are arranged into layers, which form closed vesicles, like artificial cells. A wide variety of conventional liposomes can be used with various numbers of lipid layers, size, surface charge, and lipid composition. The prolonged release rate and the reduced dispersal rate of liposomes provide a controlled administration rate of the substance at or near the administration site which gives a concentrated and prolonged accuracy of action with less systemic side effects. When administered as a lipid vesicle composition, the free ionized form of the substance also penetrates better into the tissue because of the presence of the lipid vesicles which hydrate the skin.

Occasionally, the lipid vesicle is a multilamellar lipid vesicle (MLV) which is composed of a number of bimolecular lamellae interspersed with an aqueous medium. And, sometimes the lipid vesicle is a unilamellar vesicle which is composed of a single spherical lipid bilayer entrapping aqueous solution; or, the lipid vesicles are multivesicular that is composed of a number of vesicles.

The terms "encapsulated" or "captured" refers to the capture of a substance by a lipid vesicle in some way. This includes entrapment within the enclosed lipid bilayer either by fusing smaller vesicles around the substance or transmission through the membrane or forming the lipid vesicle within the solution containing the substance or incorporation into, or binding the substance to the lipid vesicles membrane itself. The substances can have varying degrss of lipophilicity.

As used herein "cosmetic" means any material used relating to appearance or adornment or for making beauty. While use of a cosmetic is primarily to the face, such use is not a limitation as cosmetics can be applied to other areas of the body such as hands, arms, legs, feet, abdomen and the like, wherever wrinkle and/or fine line reduction is desired.

Most, if not all, known liposome suspensions are not thermodynamically stable. Instead, the liposomes in known suspensions are kinetically trapped into higher energy states by the energy used in their formation. Energy may be provided as heat, sonication, extrusion, or homogenization. Since every high-energy state tries to lower its free energy, known liposome formulations experience problems with aggregation, fusion, sedimentation and leakage of liposome associated material. A thermodynamically stable liposome formulation which could avoid some of these problems is therefore desirable.

The present description teaches liposome suspensions which are thermodynamically stable at the temperature of formation. The formulation of such suspensions is achieved by employing a composition of lipids having several fundamental properties. First, the lipid composition preferably has packing parameters which allow the formation of liposomes. Second, as part of the head group, the lipid should include polyethyleneglycol (PEG) or any polymer of similar properties which sterically stabilizes the liposomes in suspension. Third, the lipid should have a melting temperature which allows it to be in liquid form when mixed with an aqueous solution.

By employing lipid compositions having the desired fundamental properties, little or no energy need be added when mixing the lipid and an aqueous solution to form liposomes. When mixed with water, the lipid molecules disperse and self assemble as the system settles into its natural low free energy state. Depending on the lipids used, the lowest free energy state may include small unilamellar vesicle (SUV) liposomes, multilamellar vesicle (MLV) liposomes, or a combination of SUVs and MLVs.

Lipid compositions suitable for use in the invention may include compositions comprising only a single type of lipid molecule as well as compositions made up of more than one lipid. As will be appreciated by those skilled in the art, both types of compositions may be quantified according to cited fundamental properties.

Surface Charge

In the present method, the lipid vesicles preferably have a positive and/or negative surface charge which enhance their penetration as a result of the application of a particular voltage. Because of the surface charge, the penetration can be greatly increased by the present method. For example, if the lipid vesicles have a positive surface charge, a positive electric current is appropriate to aid in penetration or permeation of the skin. Conversely, if the lipid vesicles have a negative surface charge, a negative electric current is appropriate to aid in penetration. Occasionally an alternating current is applied, under these circumstances the lipid vesicle may frequently have a positive surface charge, but occasionally the lipid vesicle may have a negative surface charge. Sometimes when an alternating current is applied the composition comprises a mixture of lipid vesicles with positive surface charges and negative surface charges. Occasionally, the composition comprises polar lipid vesicles with both a positive and negative surface charge.

The preparation of lipid vesicles is well known in the art, including U.S. Pat. Nos. 4,485,054; 4,761,288; 4,937,078 and "Liposome Technology," Vols. I, II and III (1984) G. Gregoriadis ed., CRC Press, Boca Raton, Fla. Any ionized moiety having a positive or negative charge and capable of being incorporated into the lipid bilayer or bound to the surface of the lipid vesicle by conventional methods known to those of skill in the art (i.e., electrostatic attachment) for entrapping and/or binding substances to lipid vesicles, and otherwise inert to the material encapsulated for delivery to the subject, can be included in the preparation of the lipid vesicle. Such moieties are described herein are imparting a "surface charge" or "charged surface" to a subsequently or simultaneously formed lipid vesicle. Non-limiting examples of such substances which may impart a positive (+) charge include amines, such as stearylamine, in addition other compounds which may impart a positive charge include, for example, N,N-dimethyl-N-octadecyl-1-octadecanammonium choloride (bromide) (DODAC(B)), 3B[N,(N',N'-dimethylaminoethane)-carbomoyl]cholesterol (DC-Chol), dioctadecyl amido glycyl spermine (DOGS), 1,2-diacyl-3-trimethylammonium propane (DOTAP), [2,3-bis(oleoyl)propyl] trimethyl ammonium chloride (DOTMA), and tetramethyl tetra palmityl spermine (TMTPSp). Examples such substances which may impart a negative (−) charge include, for example, esters of inorganic acids, such as dicetyl phosphate, natural or synthetic lipids, such as phosphatidylserine, phosphatidylglycerol, phosphatidic acid, phosphatidylinositol, cardiolipin, and the like.

Packing Parameters

One property is the ability to form liposomes by virtue of having the proper packing parameters. Packing parameters are relative measures of a given lipid composition, and depend on factors such as size relationships between lipid head groups and lipid hydrocarbon chains, charge, and the presence of stabilizers such as cholesterol. (Israelachvili, DD Lasic, Liposomes: From Physics to Applications, Elsevier, pp 51, 1993).)

To form a lipid bilayer, lipid head groups and hydrocarbon chains preferentially organize themselves so that the radius of curvature results in a liposome (see FIG. 1). If the hydrocarbon chains are too small relative to the head group, the radius of curvature will be too large and micelles will be produced (see FIG. 3). If the hydrocarbon chains are too large relative to the head groups, the radius of curvature will be of the opposite sign and liposomes cannot form (see FIG. 4).

FIG. 1 is a diagram depicting the cross-section of a liposome made of lipid molecules. Liposome 10 comprises a lipid bilayer, made of lipid molecules (e.g., 12, 14, 16, 18), enclosing an aqueous space 20.

Figure 2:
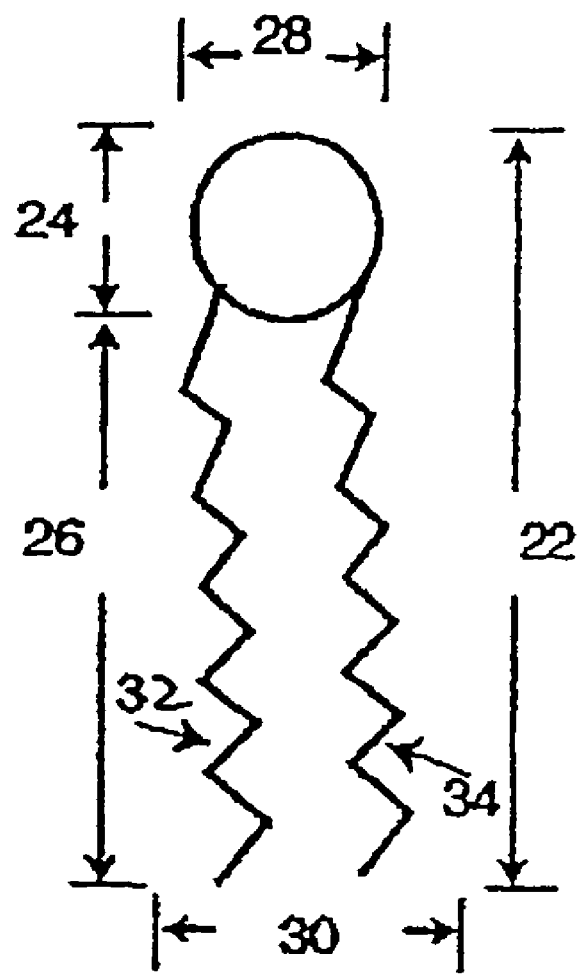
FIG. 2 is a space-filling diagram of a lipid molecule having a polar head group and nonpolar hydrocarbon chains.

FIG. 2 is a space-filling diagram of a lipid molecule having a' polar head group and nonpolar hydrocarbon chains. Lipid molecule 22 is comprised of a hydrophilic group 24 and a hydrophobic tail 26. Hydrophobic tail 26 may comprise two hydrocarbon chains 32, 34. While its chemical bonds allow the lipid molecule to be flexible, the head group generally fills an area of diameter 28 while the tail fills an area of diameter 30. Because lipid molecules generally are organized in a bilayer to form a liposome, the ratio of the head group diameter to the tail diameter can be neither too large nor too small if liposome formation is to occur.

Figure 3:
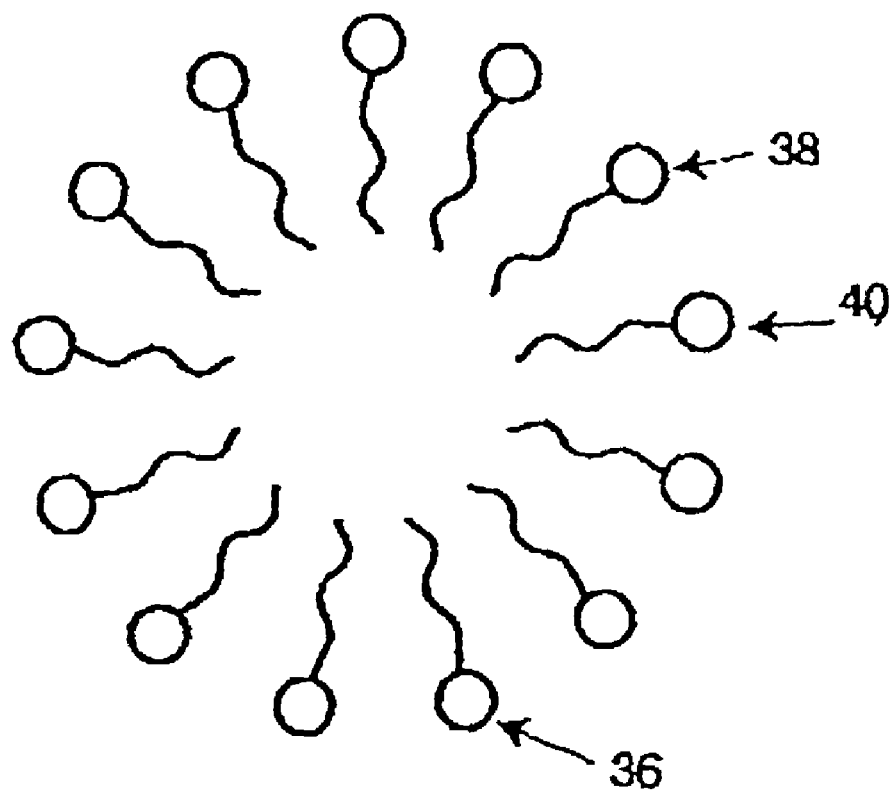
FIG. 3 is a diagram depicting a cross-section of a micelle made of lipid molecules.

FIG. 3 is a diagram depicting a cross-section of a micelle made of lipid molecules. Micelle 36 is composed of lipid molecules (e.g., 38, 40). Because the tail groups of the lipid molecules have small diameters relative to the head groups, the lipid molecules organize with a small radius of curvature, and a bilayer cannot form.

Figure 4:
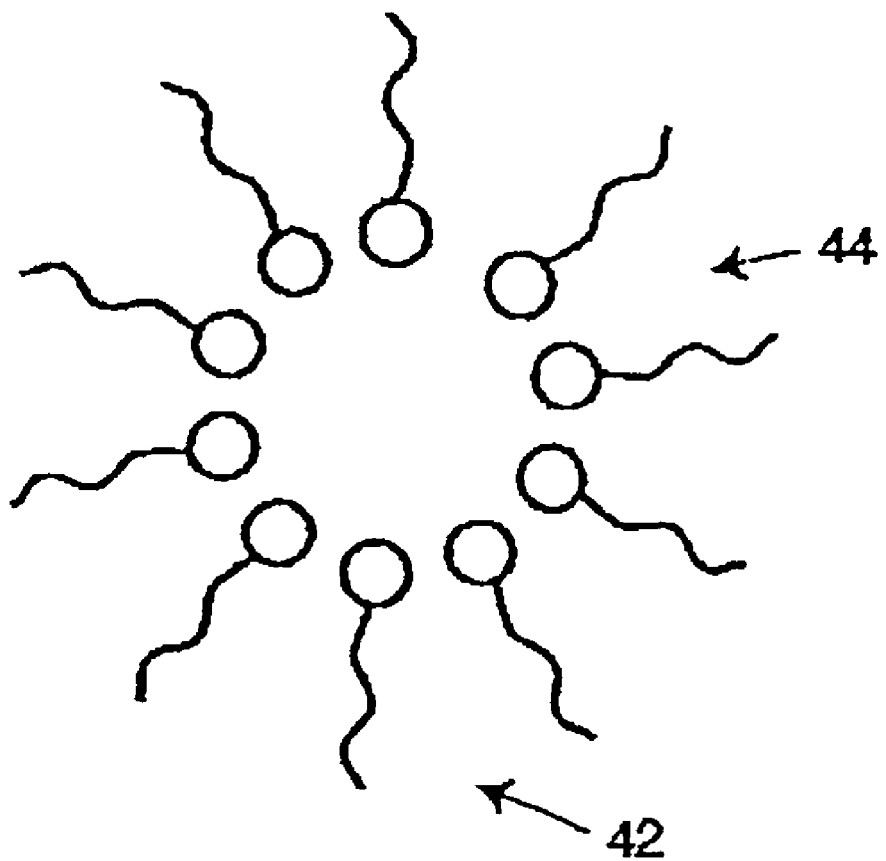
FIG. 4 is a diagram depicting a cross-section of a structure made of lipid molecules with large tails relative to the head groups.

FIG. 4 is a diagram depicting a cross-section of a structure made of lipid molecules with large tails relative to the head groups. In FIG. 4, it can be seen that structure 42 forms when lipids (e.g., 44) having large tails relative to the head groups are mixed in aqueous solution. Again, the size ratio between head groups and tails makes bilayer formation impossible.

While FIGS. 1, 3 and 4 have illustrated the basic principle of packing parameters using a single type of lipid molecule, it will be appreciated that the same principle applies to mixtures of lipids. For example, a lipid which has hydrocarbon chains too small to form liposomes as a single species can be mixed with cholesterol to result in a composition which has the proper packing parameters. As another example, a lipid which by itself has the proper packing parameters may form liposomes incorporating limited amounts of other lipids which, by themselves, do not have proper packing parameters. Both single lipids and mixtures of lipids have packing parameters that may be calculated by known methods. (ref) In general, liposome compositions which allow liposome formation have packing parameter measurements of $P_v$ between about 0.84 and 0.88 and $P_a$ between about 0.88 and 0.93.

$P_a$ is the packing parameter with respect to surface and $P_v$ is packing parameter with respect to volume (DD Lasic, Liposomes: From Physics to Applications, Elsevier, and pp 51, 1993). The parameters are derived from the equations $HC_a/T_a = P_a$ and $HC_v/T_v = P_v$ where $HC_a$ is the hydrocarbon chain area $T_a$ is the total area of the molecule, $HC_v$ is the a volume of the hydrocarbon chains and $T_v$ is the volume of the whole molecule.

Packing parameters can be calculated for mixtures of lipids, since ideal mixing of lipids results in arithmetic average of their individual characteristics. For instance $HC_a/T_a = P_a$ of a binary mixture, in the case of ideal mixing can be expressed as:

$$<P_a> = X_1 P_1 + X_2 P_2, X_1 + X_2 = 1$$

More generally, in the case of i lipids composing a given mixture, these may be represented by:

$$<P_a> = \Sigma_i X_i P_i \text{ and } \Sigma_i X_i = 1$$

where $X_i$ the mole fraction of the lipid in the mixture and $P_i$ is the packing parameter with respect to surface of that lipid.

Figure 5:
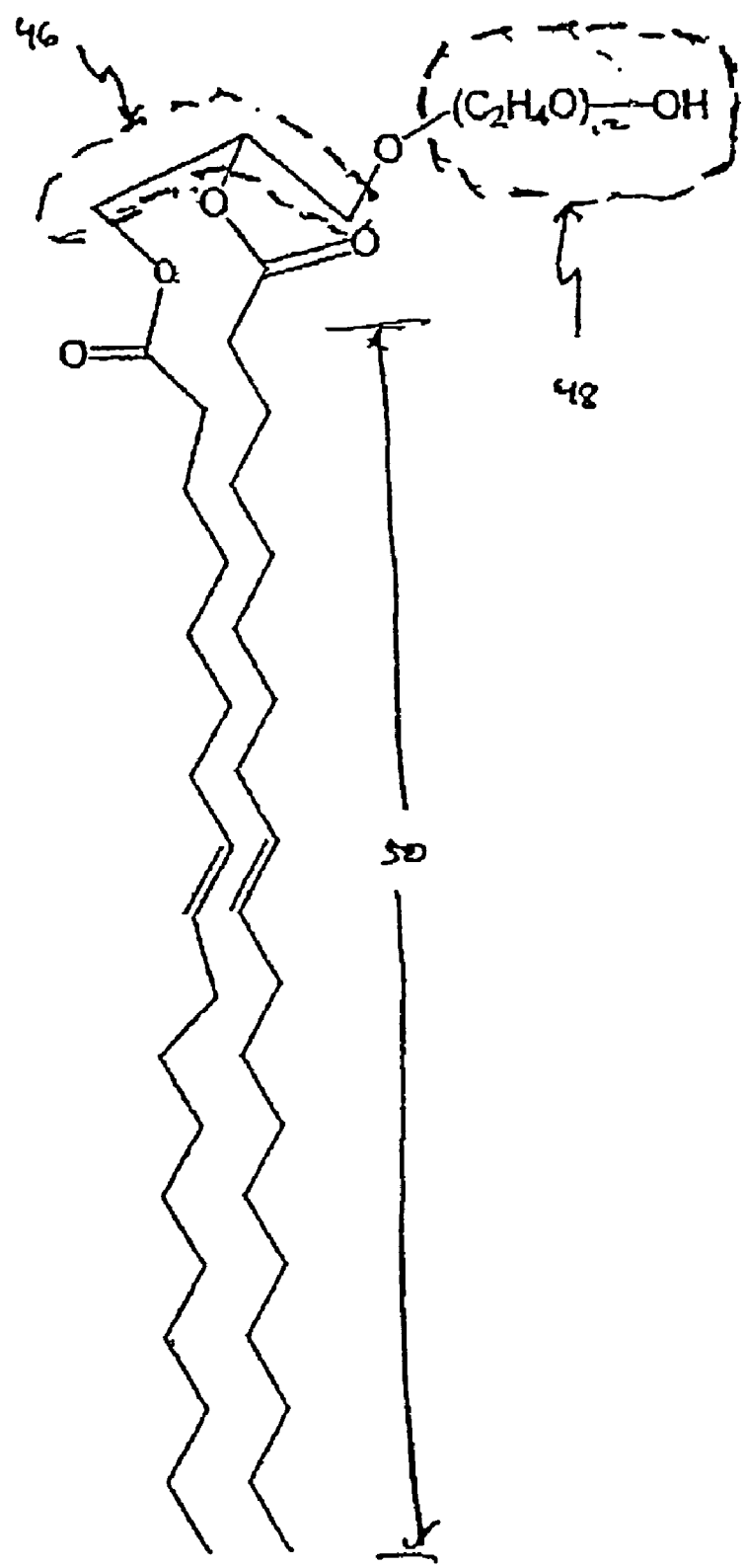
FIG. 5 is a diagram showing the molecular structure of PEG-12 Glyceryl Dioleate.
Figure 6:
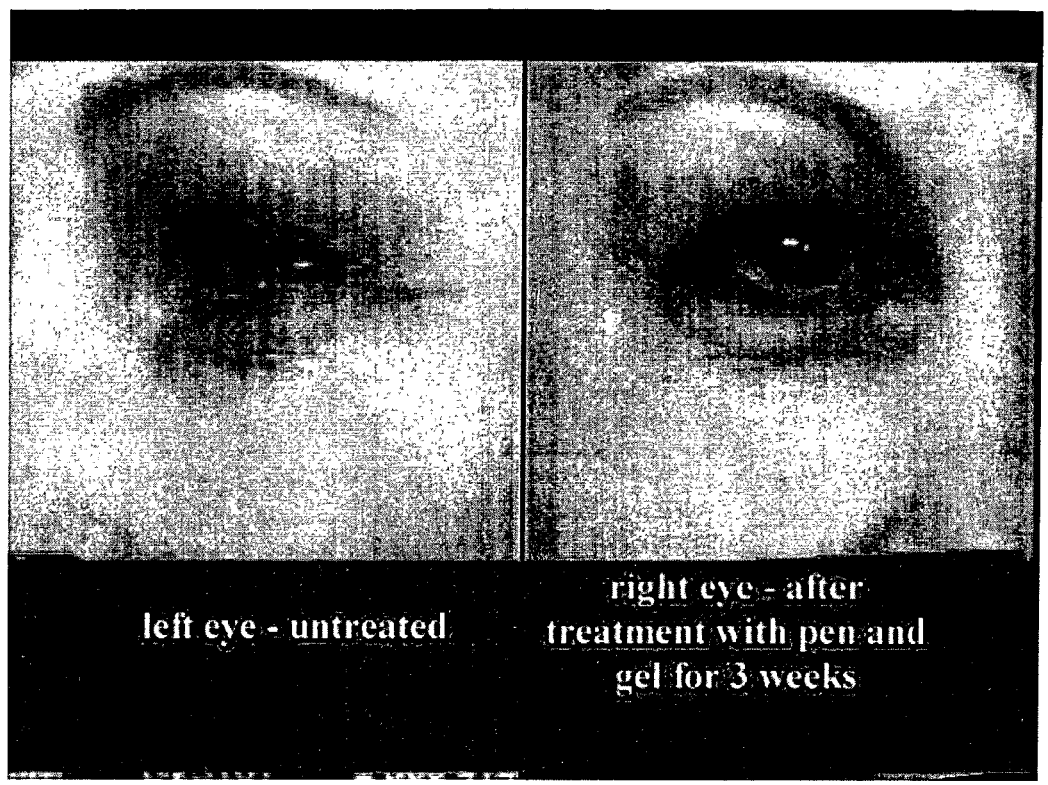
FIG. 6 presents photographs of the left and right eye of a subject after use of the presently described composition (as shown in Table 4) and device (which together comprise the present methods) for a three week period. During these three weeks the present methods were used around the right eye of the subject and not used around the left eye. In comparison with the right eye, which resembled the photo of the left eye prior to treatment, the area around the right eye exhibits a noticeable reduction in laugh lines just to the right of the eye. In addition, lines under the right eye are reduced in comparison with the left eye.

FIG. 5 is a diagram showing the molecular structure of PEG-12 Glyceryl Dioleate or Hetoxamate GDO-12 which includes a glycerol backbone 46, a PEG chain 48, and a tail group 50 having two hydrocarbon chains. Together, the backbone 46 and the PEG chain 48 comprise the head group of the molecule. PEG-12 GDO is a preferred lipid molecule for use in the present invention, in part because its head group has the proper size in relation to its tail group.

Two general factors influence the size of the head group in a lipid molecule. One is the actual physical size of the head group. For example, employing a longer PEG chain would make the head group larger. The other is the charge associated with the head group. For example, if the PEG chain was conjugated to the backbone by a phosphodiester bond the phosphate would impart a charge to the head group, effectively increasing its size. In the present invention, non-phospholipids are preferred so that the general means of varying head group size is by varying the length of the PEG chain. However, those skilled in the art will recognize that the effective size of the head group could be varied in other ways, for example by using a different backbone other than glycerol or adding a linker such as phosphate between the glycerol backbone and the PEG chain.

The size of the tail of a lipid is mostly influenced by the length of hydrocarbon chains and degree of saturation in the lipid chain. Single chain lipids will generally not form liposomes, though they may be incorporated into liposomes composed of lipids with two chains. Similarly, lipids with one long chain and one short chain may have relatively small tail size. Those skilled in the art will recognize that such lipids may be used to form liposomes in the present invention, especially if sterols such as cholesterol are used- to stabilize the bilayer.

Polyethylene Glycol Chain

A second property of lipid compositions suitable for use in the present description is that the head group of one or more lipids preferably includes a PEG chain. PEG stabilizes the liposomes by creating a steric barrier at the outer surface of the liposomes. Preferably, the PEG chain has a molecular weight between about 300 daltons and 5000 daltons, although those skilled in the art will recognize that differing concentrations of PEG on the liposome surface as well as differing chain lengths may be used to stabilize the liposomes.

Melting Temperature

A third lipid property is that the lipid composition preferably has a melting temperature which allows the composition to be in liquid form when mixed with an aqueous solution. Generally, this means that the lipid composition should have a phase transition temperature of between about 0° C. and 100° C. As with packing parameters, melting temperatures may be determined for mixtures of lipids.

Related to the melting point of a lipid is a bending elastic modulus. Generally preferred in the present invention are lipids with a bending elastic modulus that allows the lipid to be sufficiently flexible to form liposomes in an aqueous solution without the need for large energy inputs. If the bending elastic modulus is too great, the lipid will be too rigid to spontaneously form liposomes in an aqueous solution. Preferably, the bending elastic modulus is between about 0 kt and 15 kt. More preferably, the bending elastic modulus—is between about 1 kt and 10 kt. The bending elastic modulus is largely determined by the backbone. Glycerol provides an ideal backbone for the present invention.

Specific Lipids

Table 1 shows a number of lipids which have been tested as single lipids for suitability for the present invention. Lipids were tested at 2 weight percent in aqueous solution. Note that GDL means glycerol dilaurate, GDO means glycerol dioleate, GDM means glycerol dimyristate, GDP means glycerol dipalmitate, and GDS means glycerol distearate. For each lipid, the number after "PEG" indicates the numbers of $C_2H_4O$ subunits in the PEG chain. The unsaturated dioleate lipids have similar packing parameters to the saturated dimyristate lipids.

TABLE 1

| Lipid | Melting point (° C.) | $P_a$ | $P_v$ | Spontaneous Liposomes at 20° C. | Spontaneous Liposomes at 37° C. | Spontaneous Liposomes at 60° C. |
|---|---|---|---|---|---|---|
| PEG-23 GDL | Fluid @ 25 | .829 | .869 | NO | NO | NO |
| PEG-12 GDO | Fluid @ 25 | | | YES | YES | YES |
| PEG-23 GDO | Fluid @ 25 | | | NO | NO | NO |
| PEG-45 GDO | 36.3 | | | NO | NO | NO |
| PEG-12 GDM | Fluid @ 25 | .853 | .889 | YES | YES | YES |
| PEG-23 GDM | Fluid @ 25 | .837 | .875 | NO | NO | NO |
| PEG-45 GDM | 33.2 | .823 | .863 | NO | NO | NO |
| PEG-23 GDP | 31.2 | .843 | .880 | | YES | YES |
| PEG-45 GDP | 41.8 | .828 | .867 | NO | NO | NO |
| PEG-12 GDS | 40.0 | .869 | .901 | NO | NO | YES |
| PEG-23 GDS | 39.8 | .849 | .885 | NO | NO | YES |
| PEG-45 GDS | 40.8 | .830 | .870 | NO | NO | NO |

The above table shows that lipids which possess the required properties will spontaneously form liposomes when mixed in an aqueous solution. For example, PEG-12 GDM spontaneously forms liposomes at all temperatures tested since it is a liquid at those temperatures and includes PEG in addition to having packing parameters within the required ranges. Similarly, PEG-12 GDO, which shares nearly identical properties to PEG-12 GDM, spontaneously forms liposomes at all temperatures tested.

PEG-12 GDS shows one example of the requirement that the lipid be liquid at the temperature of liposome formation. While this lipid has the required packing parameters as well as including PEG, it does not spontaneously form liposomes until the temperature of liposome formation is high enough for the lipid to be in liquid form.

The GDM series of lipids illustrates the importance of proper packing parameters. While these lipids all include PEG and are in liquid form at 60 degrees, only PEG-12 GDM has the proper packing parameters to allow spontaneous liposome formation. The GDS lipid series at 60 degrees illustrates the same point.

Those skilled in the art can practice the present invention by using knowledge of the required properties to predict and create lipid compositions which will spontaneously form liposomes. For example, certain PEG lipids which form micelles can form liposomes in mixtures with sterols, such as cholesterol, because of cholesterol's effect on packing parameters and melting point. For instance, the mixture of PEG-45 GDS and cholesterol forms liposomes. Similarly, the size of the head group may be changed to affect packing parameters, for example by varying the size of the PEG chain or by varying the concentration of PEG-containing lipids in the lipid composition.

It will be appreciated that, while liposomes form spontaneously at the temperature of formation, cooling of liposomes after formation results in liposomes in trapped kinetic states. To minimize distortions in liposome structure upon such cooling, sterols such as cholesterol may be mixed with the lipid before liposome formation. It has been observed that cholesterol may be dissolved in PEG-12 GDO at up to about 10 percent by weight.

Since the liposomes of the present invention are self-forming, liposome preparation entails merely mixing the lipid with an aqueous solution. In general, liposome formation is scale dependant. It is simple, in the case of the present invention, to scale up from test batches to large batches.

Because the liposomes of the present invention exist in the lowest energy state that the lipid can exist in while in aqueous solution, reproducibility of liposome formation is no problem. A defined lipid, lipid mixture, or lipid/compound mixture will form similar liposomes every time when mixed with the same aqueous solution. It should be noted, however, that above critical concentrations (around 20% weight to volume for most lipids) non-liposomal structures will begin to form in aqueous solution.

Aggregation and fusion may occur with liposomes in thermodynamically trapped states. Because the liposomes of the present invention are in the lowest energy state, they do not aggregate and fuse.

Because the liposomes of the present invention are small, they can be sterile filtered. Also, the lipids may be heat sterilized prior to liposome formation.

As with any liposome dispersion, these liposomes can be lyophilized in the presence of appropriate cryoprotectants. Even in liquid form, the liposomes are colloidally stable because they are a thermodynamically stable system. Also, because of their self-forming nature, the liposomes need not be stored at all. Instead, the lipid may be stored and constituted into liposomes as needed.

Applications of the present liposomes include the delivery of cosmetic ingredients.

Since the liposomes include an aqueous space, a hydrophobic region within the bilayer, and sites for covalent attachment (e.g., on the PEG chain or the backbone), many types of compounds may be encapsulated by the liposomes. Such compounds include compounds ranging from hydrophilic to hydrophobic, including many insoluble compounds. These liposomes may substitute for currently available Cremophor® and Solutol®.

In one aspect, the invention includes a method of preparing liposomes. The method comprises providing an aqueous solution; providing a lipid solution, where the solution has a $P_a$ between about 0.84 and 0.88, a $P_v$ between about 0.88 and 0.93, and where the one or more lipids in the solution include a polyethyleneglycol (PEG) chain; and combining the lipid solution and the aqueous Solution. Kinetic energy, such as shaking or vortexing, may be provided to the lipid solution and the aqueous solution. The lipid solution may comprise a single lipid. The lipid may comprise dioleolglycerol-PEG-12, either alone or as one of the lipids in a mixture. The method may further comprise providing an active substance; and combining the active substance with the lipid solution and the aqueous solution.

In another aspect, the provided herein is a liposome suspension. The suspension-comprises one or more lipids, where the lipids as an aggregate have a $P_a$ between about 0.84 and 0.88, a $P_v$ between about 0.88 and 0.93 and a melting temperature of between about 0 to 100 degrees centigrade; and where the one or more lipids include a polyethyleneglycol (PEG) chain. The PEG chain preferably has a molecular weight between about 300 Daltons and 5000 Daltons. The suspension may comprise a single lipid. The lipid may comprise dioleolglycerol-PEG-12. The suspension may further comprise an active substance, which may be select from the group described above.

In another aspect, the invention includes a composition for combining with an aqueous solution to form a liposome suspension. The composition comprises one or more lipids, where the lipids as an aggregate have a $P_a$ between about 0.84 and 0.88, a $P_v$ between about 0.88 and 0.93 and a melting temperature of between about 0 to 100 degrees centigrade; and where the one or more lipids include a polyethyleneglycol (PEG) chain. The PEG chain preferably has a molecular weight between about 300 Daltons and 5000 Daltons. The composition may comprise a single lipid. The composition may comprise dioleolglycerol-PEG-12. The composition may further comprise an active compound selected from the group above. The composition may be provided in a sealed container, where the container also contains an inert gas to prevent oxidative degradation.

In another aspect, the invention includes a method of solubilizing an active compound. The method comprises providing a composition including one or more lipids, where the lipids as an aggregate have a $P_a$ between about 0.84 and 0.88, a $P_v$ between about 0.88 and 0.93 and a melting temperature of between about 0 to 100 degrees centigrade; and where the one or more lipids include a polyethyleneglycol (PEG) chain; providing the active compound; providing an aqueous solution; and combining the active compound, the lipid and the aqueous solution to form a liposome suspension. The method may further comprise providing kinetic energy to the liposome suspension. The method may include providing the composition in a sealed container containing an inert gas. The PEG chain preferably has a molecular weight between about 300 Daltons and 5000 Daltons. The composition may comprise a single lipid. The lipid may comprise dioleolglycerol-PEG-12. The active compound may be selected from the group above.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

Active Substances

Substances that can be transported into or through the tissue of a subject include any of a wide variety of cosmetic, diagnostic and biologically-active materials which can be encapsulated within a lipid vesicle. Some substances can have different uses depending on the circumstances and dose. Non-limiting examples of cosmetic ingredients occasionally used in the present invention may include vitamins, botanicals, antioxidants, nutrients, coenzymes, perfumes, moisturizers, sunscreens, suntan agents, proteins, peptides, nucleic acids, anti-inflammatories, biological and immunologic agents, dermatologic agents (such as soluble collagen and Vitamins A and E), nutrients and nutritional agents, endocrine and metabolic agents, appearance modifying agents, and the like. Examples of cosmetic ingredients can be vitamin A, C, D and/or E, alpha-hydroxy acids such as pyruvic, lactic or glycolic acids, beta-hydroxy acids, caffeine, theobromine, theophylline, aloe vera, copper peptides, zinc and its salts, calcium glucorate, tea extracts, grapeseed extracts, anti-aging agents, and the like. Both Vitamin A and E are frequently used in the present compositions because the positive stimulating effect of Vitamin A on the collagen support network and the powerful antioxidant capacity of Vitamin E and its ability as a free radical scavenger. As is known to those skilled in the art, these vitamins aid in stimulating collagen production and help to rebuild the collagen network.

As provided above, the active substance may be selected from the group comprising proteins, peptides, nucleic acids, anti-inflammatories, biological and immunologic agents, dermatologic agents (such as soluble collagen and Vitamins A and E), nutrients and nutritional agents, endocrine and metabolic agents.

The substance encapsulated within the lipid vesicle can be administered in a pharmaceutically acceptable carrier. Non-limiting examples of suitable pharmaceutically acceptable carriers that are compatible with the biological mileu of the skin are well known in the art and include buffers, such as isotonic phosphate buffer saline (PBS), carriers for topical administration of pharmaceuticals and cosmetics including liquids, water, creams, oils, lotions, ointments, gels, solids, masks, make-up bases and the like.

Sometimes the composition can be dispersed in a hydrocolloid, preferably by forming the multilamellar vesicles in the presence of an aqueous solution containing a hydrocolloid. By "hydrocolloid" or "hydrogel" or "gel" as used herein is meant any chemical substance which exhibits the ability to swell in water, retaining a significant amount of water within its structure and can be inorganic or organic, such as bentonite, methylcellulose or a single or polymer compound. The hydrocolloid effects the structure and inter-relation of the lipid vesicles and effect viscosity and adhesive properties of the final product and some can also effect the tissue itself.

Occasionally, one or more additional ingredients conventionally found in pharmaceutical or cosmetics can be included with the carrier, such as thickeners, preservatives, such as anti-oxidants, emulsifiers, dispersing agents, wetting agents, stabilizers, enzymes, and the like. Suitable additional ingredients, include, superoxide dismutase, stearyl alcohol, isopropyl mystriate sorbitan monooleate, polyethylene stearate, polyethylene glycol, water, alkali or alkaline earth lauryl sulfate, octyl dimethyl-p-amino benzoic acid, uric acid, reticulin, polymucosaccharides, hyaluronic acid, lecithin, polyethylene sorbitan monooleate, or any of the topical ingredients.

While not required to practice the method of the invention, permeability enhancers conventionally known in the art can also be present, usually about 1 to about 10% by weight. Suitable permeability enhancers include fatty acid esters and fatty alcohol ethers of $C_1$-4 alkanediols, alcohols such as ethanol, dimethyl sulfoxide, polyethylene glycol monolaurate and the like.

As one of skill in the art knows, the dose and frequency of administration of a substance by the method of the invention can vary depending on a number of factors, including the substance used, the intended use, potential skin irritation side effects, the lifetime of the substance, the tissue administered to, the age, sex and weight of the subject. Following the teachings of this application, one of skill in the art knows how to evaluate these factors and determine a suitable dose and frequency of administration. By way of non-limiting illustration, the substance being administered is present in the lipid vesicle composition in an amount of about 0.0001% to about 10% by weight, usually from about 0.1% to about 5% by weight.

Administration of an Electric Voltage

Power Source

The present method can be conducted with conventional equipment using an electric voltage produced by a device containing one or a series of batteries (e.g., between about 1 to about 8 batteries). The number of batteries used in the device may vary depending on the voltage of each battery. Generally, the power source of the device is electrically coupled to one or more conducting surfaces. This electric coupling permits an electric voltage generated by the device's power source to be administered to a subject through the conducting surface(s). On occasion, the power source may be electrically coupled to the conducting surfaces through an inverter (see below).

While not seeking to be bound by theory, the number and size of batteries for use in the present invention frequently delivers a varying voltage between about 0.25 Volts to about 20 Volts to the subject. More frequently, the voltage may vary between about 0.5 Volts and about 10 Volts, or between about 1 Volt and about 4, 5, 6, 7, 8, or about 9 Volts. At least one or more batteries, such as multiple batteries in a series, may be used to produce the desired voltage. When batteries are utilized as the power source for the device, they may be situated or otherwise housed in the body of the device. Frequently, the exact field characteristics to be applied depend upon the voltage of the power source and the resistance encountered by the voltage.

Occasionally the device described above may have a power source other than batteries, which power source most frequently is comprised to deliver an electric voltage between about 0.25 Volts to about 20 Volts to the subject. And, more frequently, the voltage may vary between about 0.5 Volts and 10 Volts. Such power sources include alternating current (AC) sources or direct current (DC) power sources in addition to AC/DC power sources. Therefore, power sources contemplated in the present invention include conventional electric power sources such as home and business outlets. Such power sources generally provide about 120 Volts provided at about 60 Hz, however, the voltage may vary from about 110 Volts to about 240 Volts and the frequency may vary from about 50 to about 60 Hz. Regardless of power source utilized, devices contemplated in the present invention should be capable of delivering a voltage between about 0.25 Volts to about 20 Volts to a subject. Therefore, as the power source is varied, so should the voltage delivery means to achieve the desired voltage. Frequently, a resistor may be used to obtain the desired voltage ranges when a conventional outlet power source is utilized. Occasionally, the power source may be provided in the form of a battery or battery pack which is capable of delivering a voltage between about 0.25 Volts to about 11 Volts to the subject. Frequently, if this type of power source is used, an inverter may be used to obtain an alternating current at the desired voltage ranges. An inverter, as used herein, refers to a device capable of converting a direct electrical current to an alternating current.

One or More Conducting Surfaces

The devices contemplated herein for administering the desired voltage ranges to the skin of a subject may have may varying characteristics. In general, the desired voltage is administered via one or more conducting surfaces located on the device. For example, devices contemplated herein are capable of delivering either positive or negative electric charges to a subject. Occasionally, devices contemplated in the present invention may be capable of delivering both a positive and negative charge to a subject. In these circumstances the device may be an alternating current device or the device may be capable of switching polarity through a switch on the device or reversing the arrangement of the electrodes or battery power source. For example, on occasion a device may deliver a positive charge within the desired voltage range to a subject, then when polarity is reversed through the use of a switch or equivalent mechanism or method known in the art, a negative charge may be delivered to the subject from the same device.

The one or more conducting surface(s) are comprised of a conducting material suitable for administering or conducting an electric voltage to the skin of a subject. Any material known in the art which is capable of carrying an electric current, e.g., a metal such as stainless steel, or doped polymer conductor, may be used as a conducting material in the present methods. The size and shape of the conducting surface which contacts the composition and skin (i.e., the first conducting surface) usually corresponds to the size and shape of the area to be treated and its thickness can readily be determined by those of skill in the art. The size and shape of an optional second conducting surface may vary, however it usually allows for direct contact with an area of the subject's body separate from the area contacted by the first conducting surface. Frequently, this second area comprises the hand or fingers of the subject. By way of nonlimiting example, when the first conducting surface is contacted with an area of the skin of a subject, which area may previously be contacted with a composition for reducing fine lines and/or wrinkles, the second conducting surface is simultaneously contacted with the fingers of the subject for the duration of the contact of the first surface with the skin of the subject. Frequently, the second conducting surface is directly contacted with the hand or fingers of the subject. Occasionally, the area of the skin where the second conducting surface is contacted is wetted or otherwise contacted with a fluid such as an electrolyte solution (e.g., saliva) or gel or composition capable of conducting an electric voltage. Sometimes this gel or composition comprises residual fine line and/or wrinkle reducing composition previously contacted with the area of the skin comprising the area where fine lines and/or wrinkle reduction is desired by a subject.

The devices contemplated in the present invention deliver a voltage to a subject through a conducting surface. Frequently the conducting surface delivers a positive charge to the subject. In addition, a negative charge may be delivered to a subject. In either circumstance, frequently the device utilized to deliver the voltage (where the voltage is originated and/or delivered) is a hand-held device.

Frequently, when a thick and spreadable coating of composition has been contacted with the skin or tissue, the conducting surface may contact areas of the skin or tissue not previously contacted with the composition due to spreading of the composition using the conducting surface. Therefore, the conducting surface is only contacting the areas of the skin contacted with composition.

Occasionally, the one or more conducting surfaces are contacted with the skin or tissue of a subject simultaneously with the composition. In these circumstances, the conducting surface may be optionally coated with the composition prior to contact with the skin or tissue. Further, the composition may be dispensed and contacted with the skin or tissue simultaneously to contact of the conducting surface with the skin or tissue.

On occasion, devices contemplated in the present invention may be capable of delivering a desired electric voltage to a subject while simultaneously delivering the composition. Although simultaneous delivery is not limited to a device which stores and delivers the composition, particular devices contemplated in these circumstances may involve a mechanism for storage and delivery of a composition which is integrated in the device. See e.g., U.S. Pat. Nos. 5,993,180 and 6,308,413.

Occasionally an intermediary material is contacted with the skin and in turn is in contact with the conducting surface. The intermediary material of suitable size and shape is treated with the composition usually before being placed in contact with the skin. The conducting surface is then placed in contact with the intermediary material. If the composition dries out, the intermediary material can be treated periodically with the composition being administered.

Any material suitable for making contact with the tissue and the conducting surface can be used as the intermediary material and usually is an absorbent material containing one or more layers such as textile, sponge, gauze, lint, paper, cotton and the like. A variety of intermediary materials of varying thicknesses are effective in the present methods, with the proviso that such intermediary material avoids inhibiting the transmission of the electric voltage to the composition and skin of the subject. The intermediary material can be treated with the composition in a manner conventionally known in the art, including pre-treating to obtain a solid form of the substance for subsequent solution or by applying the composition immediately before or during the method of the invention.

User Notification

Another option of devices contemplated herein is the inclusion of a mechanism which allows the subject to recognize when the device is "on," or producing an electrical voltage, and "off," or not producing an electric voltage. Mechanisms of this type are useful in the present invention because the device is preferably constructed to deliver a voltage in a range that is not felt or otherwise sensed by the subject using the device. Such mechanisms may be defined in terms of the stimulus provided such as light, vibration and/or sound. Generally, these stimuli are produced when the device is producing an electric voltage and not produced in the absence of a completed circuit which would lead to the production of an electric voltage. For example, if a vibration producing mechanism is used, when the device is "on" (meaning that an electric voltage is being produced), the device or a particular part of the device may vibrate slightly to allow the subject to recognize that the device is on. However, in cases where a vibration is used the vibration should not be large enough to disrupt the contact of the one or more conducting surfaces with the subject. Another example involves the use of a sound which may be emitted from the device when it is producing an electric voltage. In these circumstances the sound is merely to provide notice to the subject that the device is on. In the case of a light emitting device, any sort of indicator-type light known in the art may be used to provide notification to the subject that the device is on. For example, a light emitting diode may be incorporated in the body of the device, or the tip of the device may emit light, or any similar method of indicator lighting mechanism may be used.

Treatment Regimens

The reduction of fine lines and/or wrinkles occasionally requires a regimen of repeated applications of the composition and electric voltage. Each use may comprise application of the composition for reducing fine lines and/or wrinkles then subsequent administration of a voltage to the area contacted with the composition. Occasionally the administration of the composition and the voltage are concurrent. These regimen may vary over a large range in terms of frequency of use, duration of the regimen and duration of application of the voltage per use. Although no essential criteria are set to determine an appropriate regimen for a given subject, variables that may be accounted for are the area of the skin where fine line and/or wrinkle reduction is desired, the depth and elasticity of the fine lines and/or wrinkles in the desired treatment area, the time available to allocate to treatment, etc. Regular use, however has been demonstrated to reduce (and occasionally eliminate) fine lines and/or wrinkles (see Table 7 below).

By way of nonlimiting example, occasionally the wrinkle reducing composition may be contacted with an area of the skin where reduction of fine lines and/or wrinkles is desired. Subsequent to the contact of the skin with the composition, a device with one or more conducting surfaces capable of producing an electric voltage is contacted with the area of the skin contacted with the composition. The time between the initial contact of the skin with the wrinkle reducing composition and administration of the electric voltage may vary between less than one second to about ten minutes. Frequently the electric voltage is applied between about one second to about five minutes subsequent to contact of the skin with the wrinkle reducing composition. Under most circumstances, however, the electric voltage should be administered to the area contacted with the wrinkle reducing composition prior to the composition drying-out on the skin. In circumstances where the wrinkle reducing composition dries on the skin during, or prior to, administration of the electric voltage, additional composition should be applied the area where wrinkle and fine lines reduction is desired.

Subsequent to, or concurrent with, the application of the wrinkle reducing composition, an electric voltage is applied to the area contacted with the wrinkle reducing composition. The electric voltage may be applied for a particular duration frequently ranging between about thirty seconds to about thirty minutes. More frequently, the duration of any particular use of the presently described voltage may range between about one minute to about ten minutes. The preferred duration may vary depending on the length of time a subject may be able to allocate to use of the present invention, however, penetration of the liposomal composition into the skin of the subject is improved when more time is able to be allocated to any given treatment cycle.

The present invention may be used one or more times per day. For example, frequently the treatment regimen described above may be undertaken between one and three times over the course of a day or twenty four hour period. More frequently this treatment regimen is undertaken by a subject between one and two times per day.

The present invention may be used continuously over the course of days, weeks, months and years while wrinkle reduction is desired by a given subject. For example, a subject may desire between a two week to about eight week regimen on a particular area of the skin where fine line and/or wrinkle reduction is desired. In addition, a longer or shorter regimen may be allocated to a particular area of the skin where fine line and/or wrinkle reduction is desired. Results of any given treatment regimen may determine the length of use desired, thus any given treatment regimen need not be determined in advance of the first use.

Kits

The present invention also contemplates kits useful for reducing fine lines, wrinkles, or fine lines and wrinkles. Frequently such kits will include all components necessary for practicing the presently described methods such as a device, one or more representative compositions and instructions for use. Occasionally such kits may package the device and compositions separately for optional separate sale. Optionally such kits may include applicators, intermediary materials, batteries, and other components for use in the present methods.

In another aspect, the kits contemplated may comprise one or more representative compositions described herein useful for practicing the presently described methods. These kits are especially useful for subjects which own or have access to a device useful for practicing the presently described methods. In these and the above circumstances, the compositions are preferably packaged in a way which improves long term stability of the compositions and does not hinder their apportionment, such as, for example, in a tube, jar, dispensing well, or other packaging means known in the art.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

EXAMPLES

Example 1

Spontaneous Liposomes

Single lipids were tested for their ability to spontaneously form liposomes when mixed with an aqueous solution. PEG-12 GDO was obtained from Global 7 (New Jersey). All other lipids were synthesized for the experiment (see Table 1). For each experiment, water and lipid were separately equilibrated at the appropriate temperature. Two weight percent lipid was added to the aqueous solution, and the solution was analyzed for the presence of liposomes by optical light microscopy, cryo TEM, freeze fracture TEM, or hot stage microscopy. The results of the experiments are shown in Table 1 above.

Example 2

Formation of Multilamellar Liposomes with Cholesterol

Cholesterol, 10 Wt. %, was added to PEG-12 Glyceryl Dioleate and heated to about 60°-70° C., for 15-20 minutes. Water, at room temperature, was added to the heated lipid solution. The mixture was left overnight. Examination of the preparation under a optical microscopic with polarized light at 100 power and 600 power showed multilamellar liposomes in the size range of 20 nm to 40 nm. No crystals of cholesterol were observed.

Example 3

Spontaneous Liposomes as a Drug Solubilization Vehicle

TABLE 2

| Ingredient | Concentration (wt %) |
|---|---|
| cyclosporin A | 0.77 |
| PEG-12 GDO | 4.30 |
| DI Water | 95.23 |

Cyclosporin A (Sigma 49H4O66) was mixed with PEG-12 Glyceryl Dioleate by vortexing and sonication for 10 minutes. Water was added and gently mixed. Examination under optical microscope at 600 power showed mulitlamelar liposomes and crystals of cyclosporin A.

Example 4

Spontaneous Liposomes with Active Compounds for Dermatology

TABLE 3

| Ingredient | Concentration (wt) |
|---|---|
| PEG-12 GDO | 18 g |
| Betamethasone diproprionate | 50 mg |
| Cholesterol | 100 mg |
| Uniphen-23 ® | 1.5 mg |
| Water | 80.35 g |

Weighed amounts of PEG-12 Glyceryl Dioleate, Betamethasone diproprionate and cholesterol were combined and heated to 50° C. while mixing. Uniphen-23® and water were combined an heated to 50° C. When mixtures reached temperature they were commingled while stirring gently. Mixture was cooled to room temperature while stirring. Examination by optical microscope at 100× and 600× showed a suspension of multilamellar liposomes.

Example 5

Spontaneous Liposomes for Topical Formulations

Tretinoin (all-trans retinoic acid), 6 mg, was dissolved in 500 μl of PEG-12 Glyceryl Dioleate. Dissolution was complete. Distilled water, 4.5 ml, was added to the mixture and gently mixed. This yielded a concentration of 1 mg/ml. Examination by optical microscope showed multilamellar liposomes in the size range of 100 nm to 200 nm. This solution can easily be incorporated into a cream, gel or lotion dosage form.

Example 6

Representative Gel Formulations

The following tables present representative compositions for use in the present invention. Each of the compositions below in Tables 4-6 may be produced through methods known in the art and in accordance with the methods described above. The tables listed below provide examples of representative components of the type of compositions contemplated in the present description. Representative components such as Vitamin A, C and D may be used alone as the active ingredient in a composition or in any combination with each other or with other active ingredients described hereinbefore.

TABLE 4

| Ingredient | Concentration (wt %) |
|---|---|
| Purified water | 91.7 |
| PEG-12 Glyceryl Dioleate | 5.0 |
| Stearylamine | 0.5 |
| Cholesterol | 0.1 |
| Phenoxyethanol | 1.0 |

TABLE 4-continued

| Ingredient | Concentration (wt %) |
|---|---|
| Imidazolidinyl urea | 0.3 |
| Triethanolamine | 0.3 |
| Methylparaben | 0.25 |
| Carbomer 940 | 0.25 |
| Tocopheryl Acetate (Vitamin E) | 0.1 |
| Propylparaben | 0.05 |
| Retinyl Palmitate (Vitamin A) | 0.45 |

Table 5, below, provides another representative composition for use in the presently described methods.

TABLE 5

| Ingredient | Concentration (wt %) |
|---|---|
| Purified water | 77.15 |
| PEG-12 Glyceryl Dioleate | 15.0 |
| Hydroxyethyl Cellulose | 1.5 |
| Ascorbic Acid (Vitamin C) | 4.0 |
| Stearyl amine | 1.0 |
| Cholesterol | 0.75 |
| Polysorbate 80 | 0.2 |
| Methylparaben | 0.25 |
| Propylparaben | 0.05 |
| Butylparaben | 0.1 |

Table 6 below provides an additional example of a representative composition useful for reducing fine lines and/or wrinkles.

TABLE 6

| Ingredient | Concentration (wt %) |
|---|---|
| Purified water | 89.95 |
| PEG-12 Glyceryl Disterate | 5.0 |
| Magnesium ascorbyl phosphate (Vitamin C (form of)) | 0.50 |
| Retinol (Vitamin E (form of)) | 0.20 |
| Cholesterol | 0.25 |
| Stearylamine | 0.50 |
| Dimethicone | 2.0 |
| Tocopheryl Acetate (Vitamin B) | 1.0 |
| Methylparaben | 0.25 |
| Propylparaben | 0.05 |
| Imidazolidinyl urea | 0.30 |

Example 7

Cosmetic Treatment Process—Illustrative Results

Twelve subjects were provided the presently described composition useful for reducing fine lines and/or wrinkles (as shown in Table 4) and a representative device (described above) for administering an electric voltage. The device provided to the subjects produced a voltage in the range of about 0.5 volts to about 10 volts. The subjects used the combination of the device and composition on various areas of their skin where fine line and/or wrinkle reduction were desired. In addition, varying regimens were undertaken by each subject throughout the use of the device/composition combination. As provided in Table 7 below, a variety of positive results were achieved through the use of the device/composition combination. Generally, fine lines were reduced or removed in each subject and wrinkles were softened.

TABLE 7

| Age | Regimen | Frequency of Use (times/day) | Duration per use (minutes) | Time of Use (weeks) | Treatment Area | Results |
|---|---|---|---|---|---|---|
| 80 | Applied Gel then used pen | 2 | 5 | 3½ | lips/mouth | lines are softer; lipstick no longer bleeds |
| 52 | same | 2 | 8-10 | 3 | eyes, lips/mouth | some noticeable results |
| 60 | same | 2 | 5 | 4 | eyes, lips/mouth | lips plumped up immediately |
| 65 | same | 1-2 | 10 | 2½ | eyes and laugh lines | some improvement, "works great" and "loves" the product |
| 62 | same | 2 | 10 | 3 | forehead, eyes & mouth | has seen results, very satisfied with product |
| 65 | same | 1-2 | 7-8 | 3 | eyes, mouth & between eye brows | fine line improvement- still working on deep lines |
| 59 | same | 2 | 5 | 4 | eyes & mouth | lines are softer |
| 66 | same | 2 | 7 | 3 | eyes, mouth & forehead | noticeable improvement, will continue using for further improvement |
| 50 | same | 2 | 3 | 2 | eyes & forehead | unbelievable results - lines are gone around eyes |
| 56 | same | 1-2 | 1-2 | 3 | eyes | still working |
| 48 | same | 1 | 3-4 | 4 | eyes & mouth | some improvement |

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

All references cited herein are hereby incorporated by reference in their entireties, whether previously specifically incorporated or not. As used herein, the terms "a", "an" and "any" are each intended to include both the singular and plural forms.

Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention, as set forth in the claims which follow. All publications or patent documents cited in this specification are incorporated herein by reference as if each such publication or document was specifically and individually indicated to be incorporated herein by reference. Citation of the above publications or documents is not intended as an admission that any of the foregoing is pertinent prior art, nor does it constitute any admission as to the contents or date of these publications or documents.

I claim:

1. A cosmetic method for reducing fine lines, wrinkles, or fine lines and wrinkles on an area of skin of a subject, comprising
   contacting a composition to the area of skin, wherein the composition comprises a liposome, a substance encapsulated within the liposome, wherein said liposome comprises polyethylene glycol (PEG)-12 glyceryl dioleate or PEG-12 glyceryl dimyristate in a sufficient quantity to induce spontaneously formed liposomes at 60° C. and in a quantity less than 20% weight to volume, and wherein the liposome has a net surface charge, and wherein the composition is a liposome suspension comprising one or more lipids, where the lipids as an aggregate have a $P_a$ between about 0.84 to 0.88, a $P_v$ between about 0.88 to 0.93, and wherein the substance encapsulated within the lipid vesicle comprises soluble collagen, vitamin A, vitamin C, vitamin E, glycolic acid, or a combination thereof,
   applying an electric voltage directly to said area of the skin,
   whereby the liposome with the net surface charge is iontophoretically induced into the skin or tissue, thereby reducing fine lines, wrinkles, or fine lines and wrinkles.

2. The method of claim 1 wherein the net surface charge is positive.

3. The method of claim 1 wherein the net surface charge is negative.

4. The method of claim 1, wherein the net surface charge is provided by an ionic moiety incorporated in the lipid vesicle.

5. The method of claim 4, wherein the ionic moiety is selected from the group consisting of an amine, N,N-dimethyl-N-octadecyl-1-octadecanammonium chloride (bromide) (DODAC(B)), 3B[N,(N',N'-dimethylaminoethane)-carbomoyl] cholesterol (DC-Chol), dioctadecyl amido glycyl spermine (DOGS), 1,2-diacyl-3-trimethylammonium propane (DOTAP), [2,3-bis(oleoyl)propyl]trimethyl ammonium chloride (DOTMA), and tetramethyl tetra palmityl spermine (TMTPSp).

6. The method of claim 5, wherein the amine is stearylamine.

7. The method of claim 4, wherein the ionic moiety is selected from the group consisting of a salt of an inorganic acid, phosphatidylserine, phosphatidylglycerol, phosphatidic acid, phosphatidylinositol, and cardiolipin.

8. The method of claim 7, wherein the salt of the inorganic acid is dicetyl phosphate.

9. The method of claim 1, wherein the PEG has a molecular weight between about 300 to 500 Daltons.

10. The method of claim 1, wherein the lipid is dioleoglycerol-PEG-12.

11. The method of claim 1 wherein the voltage is in the range of about 0.5 to 10 Volts.

12. The method of claim 1 wherein the electric voltage is applied for a duration between about 1 to about 10 minutes.

13. The method of claim 1 wherein the electric voltage is applied with a device having a body, one or more conductive surfaces situated on said body, and a power source.

14. The method of claim 13 wherein the power source comprises a direct or alternating current power source.

15. The method of claim 13 wherein the power source comprises one or more batteries or a series of batteries connected in a series.

16. The method of claim 13 wherein the device further comprises an inverter.

17. The method of claim 13 wherein the first of the one or more conductive surfaces are located on the distal end of the device, and the second or remainder of the conducting surfaces is/are located on the body of the device separate from the first conductive surface.

18. The method of claim 13 wherein the composition is applied directly to one or more conductive surfaces of the device and wherein the device and composition are contacted directly to an area of the skin prior to administration of the electric voltage.

19. The method of claim 1 wherein the composition is contacted with the skin simultaneously with the application of the electric voltage.

20. The method of claim 1 wherein the composition is contacted to the skin or tissue of a subject with an applicator.

21. The method of claim 1 wherein the cosmetic treatment method is performed by a subject between about 1 to 3 times per day.

22. The method of claim 1 wherein the substance encapsulated within the lipid vesicle further comprises caffeine, theobromine, theophylline, or a combination thereof.

23. The method of claim 1, wherein the liposome is PEG-12 glyceryl dioleate (PEG-12 GDO).

24. The method of claim 1, wherein the liposome is PEG-12 glyceryl dimyristate (PEG-12 GDM).

* * * * *